United States Patent

Bichon et al.

[11] Patent Number: 5,840,275
[45] Date of Patent: Nov. 24, 1998

[54] ULTRASONIC CONTRAST AGENT WITH POLYMERIC GAS OR AIR FILLED MICROBALLOONS

[75] Inventors: Daniel Bichon, Montpellier; Philippe Bussat, Collonges S/Saleve, both of France; Michel Schneider, Troinex, Switzerland

[73] Assignee: Bracco International B.V., Netherlands

[21] Appl. No.: 291,542

[22] Filed: Aug. 16, 1994

Related U.S. Application Data

[63] Continuation of Ser. No. 33,435, Mar. 18, 1993, abandoned, which is a continuation of Ser. No. 695,343, May 3, 1991, abandoned.

[30] Foreign Application Priority Data

May 18, 1990 [EP] European Pat. Off. .............. 90810367

[51] Int. Cl.⁶ ...................................................... A61B 8/13
[52] U.S. Cl. ........................................... 424/9.52; 424/9.5
[58] Field of Search .................................. 424/489, 490, 424/450, 9.52, 9.5

[56] References Cited

U.S. PATENT DOCUMENTS

| | | | |
|---|---|---|---|
| 4,089,800 | 5/1978 | Temple | 424/9.52 |
| 4,276,885 | 7/1981 | Tickner et al. | 128/660 |
| 4,569,844 | 2/1986 | Jones | 426/2 |
| 4,675,189 | 6/1987 | Kent et al. | 424/490 |
| 4,718,433 | 1/1988 | Feinstein | 424/9.52 |
| 4,774,958 | 10/1988 | Feinstein | 424/9.52 |
| 4,789,550 | 12/1988 | Hommel et al. | 424/490 |
| 4,913,908 | 4/1990 | Couvreur et al. | 424/501 |
| 4,935,246 | 6/1990 | Ahrens | 424/490 |
| 5,271,928 | 12/1993 | Schneider et al. | 424/9 |
| 5,380,519 | 1/1995 | Schneider et al. | 424/9 |
| 5,425,366 | 6/1995 | Reinhardt et al. | 128/662.02 |
| 5,531,980 | 7/1996 | Schneider et al. | 424/9.52 |
| 5,567,414 | 10/1996 | Schneider et al. | 424/9.52 |
| 5,643,553 | 7/1997 | Schneider et al. | 424/9.52 |

FOREIGN PATENT DOCUMENTS

| | | |
|---|---|---|
| 0123235 | 4/1984 | European Pat. Off. . |
| 0274961 | 7/1988 | European Pat. Off. . |
| 0324938 | 7/1989 | European Pat. Off. . |
| 80/02365 | 11/1980 | WIPO . |

OTHER PUBLICATIONS

Fessi et al, "Nanocapsule Formation by Interfacial Polymer Deposition Following Solvent Displacement" & Int. J. Pharm. 1989, vol. 55, No. 1, pp. R1–R4.

Uno et al, "A New Method of Preparing Monocored Water–Loaded Microcapsules Using an Interfacial Polymer Deposition Process", Chemical Abstracts, vol. 101, No. 10, 3 Sep. 1984, abstract No. 73818m, Columbus, Ohio, US.

Makino et al, "Preparation and in Vitro Degradation Properties of Polylactide Microcapsules", Chemical Abstracts, vol. 102, No., 24, 17 Jun. 1985, pp. 357, Abstract No. 209367u, Columbus, Ohio US.

Ganguly et al, "Structure of Hollow Polystyrene Microspheres: an SEM Study", Biochemical Abstracts, Accession No. 89286485, vol. 88, Abstract no. 11829, 1989, Philadelphia, US.

Ohara et al, "Preparation of Ethylcellulose–Polystyrene Composite Microcapsules of 2–phase Structure and Permeability of the Microcapsule Membranes Toward Phenobarbital", Biochemical Abstracts, Accession No. 85355072, vol. 80, Abstract No. 25064, 1985, Philadelphia, US.

de Jong et al, "Absorption and Scatter of Encapsulated Gas Filled Microspheres: Theoretical Considerations and Some Measurements", Ultrasonics 1992, vol. 30, No. 2, pp. 95–103.

de Jong et al, Principles and Recent Developments in Ultrasound Contrast Agents, Ultrasonics 1991, vol. 29, pp. 324–330.

Schering AB, "Ultra–Sound Contrast Agent esp. for e.g. Heart, Veins—Comprises Microparticles of a Sugar and Gas Bubbles in a Liquid Carrier", Biochemical Abstracts, Accession No. 85020020, vol. 85, Abstract No. 08371.

*Primary Examiner*—Raj Bawa
*Attorney, Agent, or Firm*—Nixon & Vanderhye

[57] ABSTRACT

Ultrasonic contrast compositions containing gas or air filled microballoons having a mean size in the range of 0.5 to 1000 microns bounded by a 50 to 500 nm thick biodegradable, interfacially deposited, synthetic polymer membrane which is deformable and resilient in an aqueous carrier liquid are described.

13 Claims, No Drawings

ULTRASONIC CONTRAST AGENT WITH POLYMERIC GAS OR AIR FILLED MICROBALLOONS

RELATED APPLICATIONS

This is a continuation of application Ser. No. 08/033,435, filed 18 Mar. 1993, abandoned, which, in turn, is a continuation of application Ser. No. 07/695,343, filed May 3, 1991, abandoned. Priority rights under 35 U.S.C. §120 are hereby claimed under all prior related U.S. applications.

BACKGROUND OF THE INVENTION

1. Field of the Invention

The present invention concerns air or gas filled microcapsules or microballoons enclosed by an organic polymer envelope which can be dispersed or suspended in aqueous media and used in this form for oral, rectal and urethral applications or for injection into living beings, for instance for the purpose of ultrasonic echography and other medical applications.

The invention also comprises a method for making said microballoons in the dry state, the latter being instantly dispersible in an aqueous liquid carrier to give suspensions with improved properties over existing similar products. Hence, suspensions of the microballoons in a carrier liquid ready for administration are also part of the invention.

2. Related Art

It is well known that microbodies or microglobules of air or a gas, e.g. microspheres like microbubbles or microballoons, suspended in a liquid are exceptionally efficient ultrasound reflectors for echography. In this disclosure the term of "microbubble" specifically designates air or gas microspheres in suspension in a carrier liquid which generally result from the introduction therein of air or a gas in divided form, the liquid preferably also containing surfactants or tensides to control the surface properties and the stability of the bubbles. In the microbubbles, the gas to liquid interface essentially comprises loosely bound molecules of the carrier liquid. The term of "microcapsule" or "microballoon" designates preferably air or gas bodies with a material boundary or envelope of molecules other than that of the carrier liquid, i.e. a polymer membrane wall. Both microbubbles and microballoons are useful as ultrasonic contrast agents. For instance injecting into the bloodstream of living bodies suspensions of gas microbubbles or microballoons (in the range of 0.5 to 10 μm) in a carrier liquid will strongly reinforce ultrasonic echography imaging, thus aiding in the visualization of internal organs. Imaging of vessels and internal organs can strongly help in medical diagnosis, for instance for the detection of cardiovascular and other diseases.

The formation of suspensions of microbubbles in an injectable liquid carrier suitable for echography can be produced by the release of a gas dissolved under pressure in this liquid, or by a chemical reaction generating gaseous products, or by admixing with the liquid soluble or insoluble solids containing air or gas trapped or adsorbed therein.

For instance, in U.S. Pat. No. 4,446,442 (Schering), there are disclosed a series of different techniques for producing suspensions of gas microbubbles in a sterilized injectable liquid carrier using (a) a solution of a tenside (surfactant) in a carrier liquid (aqueous) and (b) a solution of a viscosity enhancer as stabilizer. For generating the bubbles, the techniques disclosed there include forcing at high velocity a mixture of (a), (b) and air through a small aperture; or injecting (a) into (b) shortly before use together with a physiologically acceptable gas; or adding an acid to (a) and a carbonate to (b), both components being mixed together just before use and the acid reacting with the carbonate to generate $CO_2$ bubbles; or adding an over-pressurized gas to a mixture of (a) and (b) under storage, said gas being released into microbubbles at the time when the mixture is used for injection.

One problem with microbubbles is that they are generally short-lived even in the presence of stabilizers. Thus, in EP-A-131.540 (Schering), there is disclosed the preparation of microbubble suspensions in which a stabilized injectable carrier liquid, e.g. a physiological aqueous solution of salt, or a solution of a sugar like maltose, dextrose, lactose or galactose, is mixed with solid microparticles (in the 0.1 to 1 μm range) of the same sugars containing entrapped air. In order to develop the suspension of bubbles in the liquid carrier, both liquid and solid components are agitated together under sterile conditions for a few seconds and, once made, the suspension must then be used immediately, i.e. it should be injected within 5–10 minutes for echographic measurements; indeed, because the bubbles are evanescent, the concentration thereof becomes too low for being practical after that period.

Another problem with microbubbles for echography after injection is size. As commonly admitted, microbubbles of useful size for allowing easy transfer through small blood vessels range from about 0.5 to 10 μm; with larger bubbles, there are risks of clots and consecutive emboly. For instance, in the bubble suspensions disclosed in U.S. Pat. No. 4,446,442 (Schering) in which aqueous solutions of surfactants such as lecithin, esters and ethers of fatty acids and fatty alcohols with polyoxyethylene and polyoxyethylated polyols like sorbitol, glycols and glycerol, cholesterol, or polyoxy-ethylene-polyoxypropylene polymers, are vigorously shaken with solutions of viscosity raising and stabilizing compounds such as mono- and polysaccharides (glucose, lactose, sucrose, dextran, sorbitol); polyols, e.g. glycerol, polyglycols; and polypeptides like proteins, gelatin, oxypolygelatin and plasma protein, only about 50% of the microbubbles are below 40–50 μm which makes such suspensions unsuitable in many echographic application.

In contrast, microcapsules or microballoons have been developed in an attempt to cure some or the foregoing deficiencies. As said before, while the microbubbles only have an immaterial or evanescent envelope, i.e. they are only surrounded by a wall of liquid whose surface tension is being modified by the presence of a surfactant, the microballoons or microcapsules have a tangible envelope made of substantive material other than the carrier itself, e.g. a polymeric membrane with definite mechanical strength. In other terms, they are microspheres of solid material in which the air or gas is more or less tightly encapsulated.

For instance, U.S. Pat. No. 4,276,885 (Tickner et al.) discloses using surface membrane microcapsules containing a gas for enhancing ultrasonic images, the membrane including a multiplicity of non-toxic and non-antigenic organic molecules. In a disclosed embodiment, these microbubbles have a gelatin membrane which resists coalescence and their preferred size is 5–10 μm. The membrane of these microbubbles is said to be sufficiently stable for making echographic measurements; however it is also said that after a period of time the gas entrapped therein will dissolve in the blood-stream and the bubbles will gradually disappear, this being probably due to slow dissolution of the gelatin. Before use, the microcapsules are kept in gelatin solutions in which they are storage stable, but the gelatin needs to be heated and melted to become liquid at the time the suspension is used for making injection.

Microspheres of improved storage stability although without gelatin are disclosed in U.S. Pat. No. 4,718,433 (Feinstein). These microspheres are made by sonication (5 to 30 KHz) of viscous protein solutions like 5% serum albumin and have diameters in the 2–20 µm range, mainly 2–4 µm. The microspheres are stabilized by denaturation of the membrane forming protein after sonication, for instance by using heat or by chemical means, e.g. by reaction with formaldehyde or glutaraldehyde. The concentration of stable microspheres obtained by this technique is said to be about $8 \times 10^6$/ml in the 2–4 µm range, about $10^6$/ml in the 4–5 µm range and less than $5 \times 10^5$ in the 5–6 µm range. The stability time of these microspheres is said to be 48 hrs or longer and they permit convenient left heart imaging after intravenous injection. For instance, the sonicated albumin microbubbles when injected into a peripheral vein are capable of transpulmonary passage. This results in echocardiographic opacification of the left ventricle cavity as well as myocardial tissues.

Recently still further improved microballoons for injection ultrasonic echography have been reported in EP-A-324.938 (Widder). In this document there are disclosed high concentrations (more than $10^8$) or air-filled protein-bounded microspheres of less than 10 µm which have life-times of several months or more. Aqueous suspensions of these microballoons are produced by ultrasonic cavitation of solutions of denaturable proteins, e.g. human serum albumin, which operation also leads to a degree of foaming of the membrane-forming protein and its subsequent hardening by heat. Other proteins such as hemoglobin and collagen are said to be convenient also.

Still more recently M. A. Wheatley et al., Biomaterials 11 (1990), 713–717, have reported the preparation of polymer-coated microspheres by ionotropic gelation of alginate. The reference mentions several techniques to generate the microcapsules; in one case an alginate solution was forced through a needle in an air jet which produced a spray of nascent air filled capsules which were hardened in a bath of 1.2% aqueous $CaCl_2$. In a second case involving co-extrusion of gas and liquid, gas bubbles were introduced into nascent capsules by means of a triple-barelled head, i.e. air was injected into a central capillary tube while an alginate solution was forced through a larger tube arranged coaxially with the capillary tube, and sterile air was flown around it through a mantle surrounding the second tube. Also in a third case, gas was trapped in the alginate solution before spraying either by using a homogeneizer or by sonication. The microballoons thus obtained had diameters in the range 30–100 µm, however still oversized for easily passing through lung capillaries.

The high storage stability of the suspensions of microballoons disclosed in EP-A-324.938 enables them to be marketed as such, i.e. with the liquid carrier phase, which is a strong commercial asset since preparation before use is no longer necessary. However, the protein material used in this document may cause allergenic reactions with sensitive patients and, moreover, the extreme strength and stability of the membrane material has some drawbacks: for instance, because of their rigidity, the membranes cannot sustain sudden pressure variations to which the microspheres can be subjected, for instance during travel through the bloodstream, these variations of pressure being due to heart pulsations. Thus, under practical ultrasonic tests, a proportion of the microspheres will be ruptured which makes imaging reproducibility awkward; also, these microballoons are not suitable for oral application as they will not resist the digestive enzymes present in the gastrointestinal tract. Moreover, it is known that microspheres with flexible walls are more echogenic than corresponding microspheres with rigid walls.

Furthermore, in the case of injections, excessive stability of the material forming the walls of the microspheres will slow down its biodegradation by the organism under test and may result into metabolization problems. Hence it is much preferable to develop pressure sustaining microballoons bounded by a soft and elastic membrane which can temporarily deform under variations of pressure and endowed with enhanced echogenicity; also it might be visualized that micro-balloons with controllable biodegradability, for instance made of semi-permeable biodegradable polymers with controlled micro-porosity for allowing slow penetration of biological liquids, would be highly advantageous.

BRIEF SUMMARY OF THE INVENTION

These desirable features have now been achieved with the microballoons of the present invention as defined in the claims Moreover, although the present microspheres can generally be made relatively short-lived, i.e. susceptible to biodegradation to cope with the foregoing metabolization problems by using selected types of polymers, this feature (which is actually controlled by the fabrication parameters) is not a commercial drawback because either the microballoons can be stored and shipped dry, a condition in which they are stable indefinitely, or the membrane can be made substantially impervious to the carrier liquid, degradation starting to occur only after injection. In the first case, the microballoons supplied in dry powder form are simply admixed with a proportion of an aqueous phase carrier before use, this proportion being selected depending on the needs. Note that this is an additional advantage over the prior art products because the concentration can be chosen at will and initial values far exceeding the aforementioned $10^8$/ml, i.e. in the range $10^5$ to $10^{10}$, are readily accessible. It should be noted that the method of the invention (to be disclosed hereafter) enables to control porosity to a wide extent; hence microballoons with a substantially impervious membrane can be made easily which are stable in the form of suspensions in aqueous liquids and which can be marketed as such also.

DETAILED DESCRIPTION OF EXEMPLARY EMBODIMENTS

Microspheres with membranes of interfacially deposited polymers although in the state where they are filled with liquid, are well known in the art. They may normally result from the emulsification into droplets (the size of which is controllable in function to the emulsification parameters) of a first aqueous phase in an organic solution of polymer followed by dispersion of this emulsion into a second water phase and subsequent evaporation of the organic solvent. During evaporation of the volatile solvent, the polymer deposits interfacially at the droplets boundary and forms a microporous membrane which efficiently bounds the encapsulated first aqueous phase from the surrounding second aqueous phase. This technique, although possible, is not preferred in the present invention.

Alternatively, one may emulsify with an emulsifier a hydrophobic phase in an aqueous phase (usually containing viscosity increasing agents as emulsion stabilizers) thus obtaining an oil-in-water type emulsion of droplets of the hydrophobic phase and thereafter adding thereto a membrane forming polymer dissolved in a volatile organic solvent not miscible with the aqueous phase.

If the polymer is insoluble in the hydrophobic phase, it will deposit interfacially at the boundary between the droplets and the aqueous phase. Otherwise, evaporation of the volatile solvent will lead to the formation of said interfacially deposited membrane around the droplets of the emulsified hydrophobic phase. Subsequent evaporation of the encapsulated volatile hydrophobic phase provides water filled microspheres surrounded by interfacially deposited polymer membranes. This technique which is advantageously used in the present invention is disclosed by K. Uno et al. in J. Microencapsulation 1 (1984), 3–8 and K. Makino et al., Chem. Pharm. Bull. 33 (1984), 1195–1201. As said before, the size of the droplets can be controlled by changing the emulsification parameters, i.e. nature of emulsifier (more effective the surfactant, i.e. the larger the hydrophilic to lipophilic balance, the smaller the droplets) and the stirring conditions (faster and more energetic the agitation, the smaller the droplets).

In another variant, the interfacial wall forming polymer is dissolved in the starting hydrophobic phase itself; the latter is emulsified into droplets in the aqueous phase and the membrane around the droplets will form upon subsequent evaporation of this encapsulated hydrophobic phase. An example of this is reported by J. R. Farnand et al., Powder Technology 22 (1978), 11–16 who emulsify a solution of polymer (e.g. polyethylene) in naphthalene in boiling water, then after cooling they recover the naphthalene in the form of a suspension of polymer bounded microbeads in cold water and, finally, they remove the naphthalene by subjecting the microbeads to sublimation, whereby 25 $\mu$m microballoons are produced. Other examples exist, in which a polymer is dissolved in a mixed hydrophobic phase comprising a volatile hydrophobic organic solvent and a water-soluble organic solvent, then this polymer solution is emulsified in a water phase containing an emulsifier, whereby the water-soluble solvent disperses into the water phase, thus aiding in the formation of the emulsion of microdroplets of the hydrophobic phase and causing the polymer to precipitate at the interface; this is disclosed in EP-A-274.961 (H. Fessi).

The aforementioned techniques can be adapted to the preparation of air or gas filled microballoons suited for ultrasonic imaging provided that appropriate conditions are found to control sphere size in the desired ranges, cell-wall permeability or imperviousness and replacement of the encapsulated liquid phase by air or a selected gas. Control of overall sphere size is obviously important to adapt the microballoons to use purposes, i.e. injection or oral intake. The size conditions for injection (about 0.5–10 $\mu$m average size) have been discussed previously. For oral application, the range can be much wider, being considered that echogenicity increases with size; hence microballoons in several size ranges between say 1 and 1000 $\mu$m can be used depending on the needs and provided the membrane is elastic enough not to break during transit in the stomach and intestine. Control of cell-wall permeability is important to ensure that infiltration by the injectable aqueous carrier phase is absent or slow enough not to impair the echographic measurements but, in cases, still substantial to ensure relatively fast after-test biodegradability, i.e. ready metabolization of the suspension by the organism. Also the microporous structure of the microballoons envelope (pores of a few nm to a few hundreds of nm or more for microballoons envelopes of thickness ranging from 50–500 nm) is a factor of resiliency, i.e. the microspheres can readily accept pressure variations without breaking. The preferred range of pore sizes is about 50–2000 nm.

The conditions for achieving these results are met by using the method disclosed herein.

One factor which enables to control the permeability of the microballoons membrane is the rate of evaporation of the hydrophobic phase relative to that of water in step (4) of the method e.g. under conditions of freeze drying. For instance if the evaporation in is carried out between about −40° and 0° C., and hexane is used as the hydrophobic phase, polystyrene being the interfacially deposited polymer, beads with relatively large pores are obtained; this is so because the vapour pressure of the hydrocarbon in the chosen temperature range is significantly greater than that of water, which means that the pressure difference between the inside and outside of the spheres will tend to increase the size of the pores in the spheres membrane through which the inside material will be evaporated. In contrast, using cyclooctane as the hydrophobic phase (at −17° C. the vapour pressure is the same as that of water) will provide beads with very tiny pores because the difference of pressures between the inside and outside of the spheres during evaporation is minimized.

Depending on degree of porosity the microballoons of this invention can be made stable in an aqueous carrier from several hours to several months and give reproducible echographic signals for a long period of time. Actually, depending on the polymer selected, the membrane of the microballoons can be made substantially impervious when suspended in carrier liquids of appropriate osmotic properties, i.e. containing solutes in appropriate concentrations. It should be noted that the existence of micropores in the envelope of the microballoons of the present invention appears to be also related with the echographic response, i.e., all other factors being constant, microporous vesicles provide more efficient echographic signal than corresponding non-porous vesicles. The reason is not known but it can be postulated that when a gas is in resonance in a closed structure, the damping properties of the latter may be different if it is porous or non-porous.

Other non water soluble organic solvents which have a vapour pressure of the same order of magnitude between about −40° C. and 0° C. are convenient as hydrophobic solvents in this invention. These include hydrocarbons such as for instance n-octane, cyclooctane, the dimethylcyclohexanes, ethyl-cyclohexane, hexane, 2-, 3- and 4-methyl-heptane, 3-ethyl-hexane, toluene, xylene, 2-methyl-2-heptane, 2,2,3,3-tetramethylbutane and the like. Esters such as propyl and isopropyl butyrate and isobutyrate, butyl-formate and the like, are also convenient in this range. Another advantage of freeze drying is to operate under reduced pressure of a gas instead of air, whereby gas filled microballoons will result. Physiologically acceptable gases such as $CO_2$, $N_2O$, methane, Freon, helium and other rare gases are possible. Gases with radioactive tracer activity can be contemplated.

As the volatile solvent insoluble in water to be used for dissolving the polymer to be precipitated interfacially, one can cite halo-compounds such as $CCl_4$, $CH_3Br$, $CH_2Cl_2$, chloroform, Freon, low boiling esters such as methyl, ethyl and propyl acetate as well as lower ethers and ketones of low water solubility. When solvents not totally insoluble in water are used, e.g. diethyl-ether, it is advantageous to use, as the aqueous phase, a water solution saturated with said solvent beforehand.

The aqueous phase in which the hydrophobic phase is emulsified as an oil-in-water emulsion preferably contains 1–20% by weight of water-soluble hydrophilic compounds like sugars and polymers as stabilizers, e.g. polyvinyl alcohol (PVA), polyvinyl pyrrolidone (PVP), polyethylene glycol (PEG), gelatin, polyglutamic acid, albumin, and polysaccharides such as starch, dextran, agar, xanthan and the like. Similar aqueous phases can be used as the carrier liquid in which the microballoons are suspended before use.

Part of this water-soluble polymer can remain in the envelope of the microballoons or it can be removed by washing the beads before subjecting them to final evaporation of the encapsulated hydrophobic core phase.

The emulsifiers to be used (0.1–5% by weight) to provide the oil-in-water emulsion of the hydrophobic phase in the aqueous phase include most physiologically acceptable emulsifiers, for instance egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline. Emulsifiers also include surfactants such as free fatty acids, esters of fatty acids with polyoxyalkylene compounds like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and triglycerides of saturated or unsaturated fatty acids; glycerides or soya-oil and sucrose.

The polymer which constitutes the envelope or bounding membrane of the injectable microballoons can be selected from most hydrophilic, biodegradable physiologically compatible polymers. Among such polymers one can cite polysaccharides of low water solubility, polylactides and polyglycolides and their copolymers, copolymers of lactides and lactones such as ε-caprolactone, δ-valerolactone and, polypeptides. The great versatility in the selection of synthetic polymers is another advantage of the present invention since, as with allergic patients, one may wish to avoid using microballoons made of natural proteins (albumin, gelatin) like in U.S. Pat. No. 4,276,885 or EP-A-324.938. Other suitable polymers include poly-(ortho)esters (see for instance U.S. Pat. No. 4,093,709; U.S. Pat. No. 4,131,648; U.S. Pat. No. 4,138,344; U.S. Pat. No. 4,180,646); polylactic and polyglycolic acid and their copolymers, for instance DEXON (see J. Heller, Biomaterials 1 (1980), 51; poly(DL-lactide-co-δ-caprolactone), poly(DL-lactide-co-δ-valerolactone), poly(DL-lactide-co-δ-butyrolactone), poly-alkylcyanoacrylates; polyamides, polyhydroxy-butyrate; polydioxanone; poly-β-aminoketones (Polymer 23 (1982), 1693); polyphosphazenes (Science 193 (1976), 1214); and polyanhydrides. References on biodegradable polymers can be found in R. Langer et al., Macromol. Chem. Phys. C23 (1983), 61–126. Polyamino-acids such as polyglutamic and polyaspartic acids can also be used as well as their derivatives, i.e. partial esters with lover alcohols or glycols. One useful example of such polymers is poly-(t.butyl-glutamate). Copolymers with other amino-acids such as methionine, leucine, valine, proline, glycine, alamine, etc. are also possible. Recently some novel derivatives of poly-glutamic and polyaspartic acid with controlled biodegradability have been reported (see WO87/03891; U.S. Pat. No. 4,888,398 and EP-130.935 incorporated here by reference). These polymers (and copolymers with other amino-acids) have formulae of the following type:

$$—(NH—CHA—CO)_x(NH—CHX—CO)_y$$

where X designates the side chain of an amino-acid residue and A is a group of formula $—(CH_2)_nCOOR^1R^2—OCOR$ (II), with $R^1$ and $R^2$ being H or lover alkyls, and R being alkyl or aryl; or R and $R^1$ are connected together by a substituted or unsubstituted linking member to provide 5- or 6- membered rings.

A can also represent groups of formulae:

$$—(CH_2)_nCOO—CHR^1COOR \qquad (I)$$

and $$—(CH_2)_nCO(NH—CHX—CO)_mNH—CH(COOH)—(CH_2)_pCOOH \qquad (III)$$

and corresponding anhydrides. In all these formulae n, m and p are lower integers (not exceeding 5) and x and y are also integers selected for having molecular weights not below 5000.

The aforementioned polymers are suitable for making the microballoons according to the invention and, depending on the nature of substituents R, $R^1$, $R^2$ and X, the properties of the membrane can be controlled, for instance, strength, elasticity and biodegradability. For instance X can be methyl (alanine), isopropyl (valine), isobutyl (leucine and isoleucine), benzyl (phenylalanine).

Additives can be incorporated into the polymer wall of the microballoons to modify the physical properties such as dispersibility, elasticity and water permeability. For incorporation in the polymer, the additives can be dissolved in the polymer carrying phase, e.g. the hydrophobic phase to be emulsified in the water phase, whereby they will co-precipitate with the polymer during inter-facial membrane formation.

Among the useful additives, one may cite compounds which can "hydrophobize" the microballoons membrane in order to decrease water permeability, such as fats, waxes and high molecular-weight hydrocarbons. Additives which improve dispersibility of the microballoons in the injectable liquid-carrier are amphipatic compounds like the phospholipids; they also increase water permeability and rate of biodegradability.

Non-biodegradable polymers for making microballoons to be used in the digestive tract can be selected from most water-insoluble, physiologically acceptable, bioresistant polymers including polyolefins (polystyrene), acrylic resins (polyacrylates, polyacrylonitrile), polyesters (polycarbonate), polyurethanes, polyurea and their copolymers. ABS (acryl-butadiene-styrene) is a preferred copolymer.

Additives which increase membrane elasticity are the plasticizers like isopropyl myristate and the like. Also, very useful additives are constituted by polymers akin to that of the membrane itself but with relatively low molecular weight. For instance when using copolymers of polylactic/polyglycolic type as the membrane forming material, the properties of the membrane can be modified advantageously (enhanced softness and biodegradability) by incorporating, as additives, low molecular weight (1000 to 15,000 Dalton) polyglycolides or polylactides. Also polyethylene glycol of moderate to low $M_w$ (e.g. PEG 2000) is a useful softening additive.

Preferably the plasticizers include isopropyl myristate, glyceryl monstearate and the like to control flexibility, the amphipatic substance include surfactants and phospholipids like the lecithins to control permeability by increasing porosity while the hydrophobic compounds include molecular weight hydrocarbon like the paraffin-waxes to reduce porosity.

The quantity of additives to be incorporated in the polymer forming the inter-facially deposited membrane of the present microballoons is extremely variable and depends on the needs. In some cases no additive is used at all; in other cases amounts of additives which may reach about 20% by weight of the polymer are possible.

The injectable microballoons of the present invention can be stored dry in the presence or in the absence of additives to improve conservation and prevent coalescence. As additives, one may select from 0.1 to 25% by weight of water-soluble physiologically acceptable compounds such as mannitol, galactose, lactose or sucrose or hydrophilic polymers like dextran, xanthan, agar, starch, PVP, polyglutamic acid, polyvinylalcohol (PVA), albumin and gelatin. The useful life-time of the microballoons in the injectable liquid carrier phase, i.e. the period during which useful echographic signals are observed, can be controlled to last from a few minutes to several months depending on the needs; this can be done by controlling the porosity of the membrane from substantial imperviousness toward carrier liquids to porosities having pores of a few nanometers to several hundreds of nanometers. This degree of porosity can be controlled, in addition to properly selecting the membrane forming polymer and polymer additives, by adjusting the evaporation rate and temperature in step (4) of the method of and properly selecting the nature of the compound (mixture of compounds) constituting the hydrophobic phase, i.e. the greater the differences in its partial pressure of evaporation with that of the water phase, the coarser the pores in the microballoons membrane will be. Of course, this control by selection of the hydrophobic phase can be further refined by the choice of stabilizers and by adjusting the concentration thereof in order to control the rate of water evaporation during the forming of the microballoons. All these changes can easily be made by skilled persons without exercizing inventiveness and need not be further discussed.

It should be remarked that although the microballoons of this invention can be marketed in the dry state, more particularly when they are designed with a limited life time after injection, it may be desirable to also sell ready preparations, i.e. suspensions of microballoons in an aqueous liquid carrier ready for injection or oral administration. This requires that the membrane of the microballoons be substantially impervious (at least for several months or more) to the carrier liquid. It has been shown in this description that such conditions can be easily achieved with the present method by properly selecting the nature of the polymer and the interfacial deposition parameters. Actually parameters have been found (for instance using the polyglutamic polymer (where A is the group of formula II) and cyclooctane as the hydrophobic phase) such that the porosity of the membrane after evaporation of the hydrophobic phase is so tenuous that the microballoons are substantially impervious to the aqueous carrier liquid in which they are suspended.

A preferred administrable preparation for diagnostic purposes comprises a suspension in buffered or unbuffered saline (0.9% aqueous NaCl; buffer 10 mM tris-HCl) containing $10^8$–$10^{10}$ vesicles/ml. This can be prepared mainly according to the directions of the Examples below, preferably Examples 3 and 4, using poly-(DL-lactide) polymers from the Company Boehringer, Ingelheim, Germany.

The following Examples illustrate the invention practically.

EXAMPLES 1

One gram of polystyrene was dissolved in 19 g of liquid naphthalene at 100° C. This naphthalene solution was emulsified at 90°–95° C. into 200 ml of a water solution of polyvinyl alcohol (PVA) (4% by weight) containing 0.1% of Tween-40 emulsifier. The emulsifying head was a Polytron PT-3000 at about 10,000 rpm.

Then the emulsion was diluted under agitation with 500 ml of the same aqueous phase at 15° C. whereby the naphthalene droplets solidified into beads of less than 50 μm as ascertained by passing through a 50 μm mesh screen. The suspension was centrifugated under 1000 g and the beads were washed with water and recentrifugated. This step was repeated twice.

The beads were resuspended in 100 ml of water with 0.8 g of dissolved lactose and the suspension was frozen into a block at 31 30° C. The block was thereafter evaporated under about 0.5–2 Torr between about −20 and −10° C. Air filled microballoons of average size 5–10 μm and controlled porosity were thus obtained which gave an echographic signal at 2.25 and 7.5 MHz after being dispersed in water (3% dispersion by weight). The stability of the microballoons in the dry state was effective for an indefinite period of time: once suspended in an aqueous carrier liquid the useful life-time for echography was about 30 min or more. Polystyrene being non-biodegradable, this material was not favored for injection echography but was useful for digestive tract investigations. This Example clearly establishes the feasibility of the method of the invention.

EXAMPLES 2

A 50:50 copolymer mixture (0.3 g) of DL-lactide and glycolide (Du Pont Medisorb) and 16 mg of egg-lecithin were dissolved in 7.5 ml of $CHCl_3$ to give solution (1).

A solution (2) containing 20 mg of paraffin-wax (N.P. 54°–56° C.) in 10 ml of cyclooctane (M.P. 10°–13°) was prepared and emulsified in 150 ml of a water solution (0.13% by weight) of Pluronic F-108 (a block copolymer of ethylene oxide and propylene oxide) containing also 1.2 g of $CHCl_3$. Emulsification was carried out at room temperature for 1 min with a Polytron head at 7000 rpm. Then solution (1) was added under agitation (7000 rpm) and, after about 30–60 sec, the emulsifier head was replaced by a helical agitator (500 rpm) and stirring was continued for about 3 hrs at room temperature (22° C.). The suspension was passed through a 50 μm screen and frozen to a block which was subsequently evaporated between −20° and 0° C. under high-vacuum (catching trap −60° C. to −80° C.). There were thus obtained 0.264 g (88%) of air-filled microballoons stable in the dry state.

Suspensions of said microballoons in water (no stabilizers) gave a strong echographic signal for at least one hour. After injection in the organism, they biodegraded in a few days.

EXAMPLES 3

A solution was made using 200 ml of tetrahydrofuran (THF), 0.8 g of a 50:50 DL-lactide/glycolide copolymer (Boehringer AG), 80 mg of egg-lecithin, 64 mg of paraffin-wax and 4 ml of octane. This solution was emulsified by adding slowly into 400 ml of a 0.1 aqueous solution of Pluronic F-108 under helical agitation (500 r.p.m.). After stirring for 15 min, the milky dispersion was evaporated under 10–12 Torr 25° C. in a rotavapor until its volume was reduced to about 400 ml. The dispersion was sieved on a 50 μm grating, then it was frozen to −40° C. and freeze-dried under about 1 Torr. The residue, 1.32 g of very fine powder, was taken with 40 ml of distilled water which provided, after 3 min of manual agitation, a very homogeneous dispersion of microballoons of average size 4.5 μm as measured using a particle analyzer (Mastersizer from Malvern). The concentration of microballoons (Coulter Counter) was about $2 \times 10^9$/ml. This suspension gave strong echographic signals which persisted for about 1 hr.

If in the present example, the additives to the membrane polymer are omitted, i.e. there is used only 800 mg of the lactide/glycolide copolymer in the THF/octane solution, a dramatic decrease in cell-wall permeability is observed, the echographic signal of the dispersion in the aqueous carrier not being significantly attenuated after 3 days.

Using intermediate quantities of additives provided beads with controlled intermediate porosity and life-time.

EXAMPLES 4

There was used in this Example a polymer of formula defined in claim 8 in which the side group has formula (II) where $R^1$ and $R^2$ are hydrogen and R is tert.butyl. The preparation of this polymer (defined as poly-POMEG) is described in U.S. Pat. No. 4,888,398.

The procedure was like in Example 3, using 0.1 g poly-POMEG, 70 ml of THF, 1 ml of cyclooctane and 100 ml of a 0.1% aqueous solution of Pluronic F-108. No lecithin or high-molecular weight hydrocarbon was added. The milky emulsion was evaporated at 27° C./10 Torr until the residue was about 100 ml, then it was screened on a 50 μm mesh and frozen. Evaporation of the frozen block was carried out (0.5–1 Torr) until dry. The yield was 0.18 g because of the presence of the surfactant. This was dispersed in 10 ml of distilled water and counted with a Coulter Counter. The measured concentration was found to be $1.43 \times 10^9$ microcapsules/ml, average size 5.21 μm as determined with a particle analyzer (Mastersizer from Malvern). The dispersion was diluted 100×, i.e. to give about $1.5 \times 10^7$ microspheres/ml and measured for echogenicity. The amplitude of the echo signal was 5 times greater at 7.5 MHz than at 2.25 MHz. These signals were reproducible for a long period of time.

Echogenicity measurements were performed with a pulse-echo system consisting of a plexiglas specimen holder (diameter 30 mm) with a 20 μm thick Mylar acoustic window, a transducer holder immersed in a constant temperature water bath, a pulser-receiver (Accutron M3010JS) with an external pre-amplifier with a fixed gain of 40 dB and an internal amplifier with gain adjustable from −40 to +40 dB and interchangeable 13 mm unfocused transducers. A 10 MHz low-pass filter was inserted in the receiving part to improve the signal to noise ratio. The A/D board in the IBM PC was a Sonotek STR 832. Measurements were carried out at 2.25, 3.5, 5 and 7.5 MHz.

If in the present Example, the polymer used is replaced by lactic-lactone copolymers, the lactones being δ-butyrolactone, δ-valerolactone or ε-caprolactone (see Fukuzaki et al., J. Biomedical Mater. Res. 25 (1991), 315–328), similar favorable results were obtained. Also in a similar context, polyalkylcyano-acrylates and particularly a 90:10 copolymer poly(DL-lactide-co-glycolide) gave satisfactory results. Finally, a preferred polymer is a poly(DL-lactide) from the Company Boehringer-Ingelheim sold under the name "Resomer R-206" or Resomer R-207.

EXAMPLES 5

Two-dimensional echocardiography was performed using an Acuson-128 apparatus with the preparation of Example 4 ($1.43 \times 10^9$/ml) in an experimental dog following peripheral vein injection of 0.1–2 ml of the dispersion. After normally expected contrast enhancement imaging of the right heart, intense and persistent signal enhancement of the left heart with clear outlining of the endocardium was observed, thereby confirming that the microballoons made with poly-POMEG (or at least a significant part of them) were able to cross the pulmonary capillary circulation and to remain in the blood-stream for a time sufficient to perform efficient echographic analysis.

In another series of experiments, persistent enhancement of the Doppler signal from systemic arteries and the portal vein was observed in the rabbit and in the rat following peripheral vein injection of 0.5–2 ml of a preparation of microballoons prepared as disclosed in Example 4 but using poly(DL-lactic acid) as the polymer phase. The composition used contained $1.9 \times 10^8$ vesicles/ml.

Another composition prepared also according to the directions of Example 4 was achieved using poly (tert.butylglutamate). This composition (0.5 ml) at dilution of $3.4 \times 10^8$ microballoons/ml was injected in the portal vein of rats and gave persistent contrast enhancement of the liver parenchyma.

EXAMPLES 6

A microballoon suspension ($1.1 \times 10^9$ vesicles/ml) was prepared as disclosed in Example 1 (resin=polystyrene). One ml of this suspension was diluted with 100 ml of 300 mM mannitol solution and 7 ml of the resulting dilution was administered intragastrically to a laboratory rat. The animal was examined with an Acuson-128 apparatus for 2-dimensional echography imaging of the digestive tract which clearly showed the single loops of the small intestine and of the colon.

We claim:

1. An ultrasonic contrast agent comprising a suspension of air or gas microballoons in a physiologically acceptable aqueous carrier liquid in a concentration of $10^5$ to $10^{10}$ microballoons/ml, the microballoons having a mean size in the range of 0.5 to 1,000 microns, are bounded by a soft, elastic, 50–500 nm thick polymer membrane filled with air or a physiologically acceptable gas, the membrane being temporarily deformable under pressure variations and made from a biodegradable, synthetic, resilient, interfacially depositable polymer selected from the group consisting of polysaccharides, polylactides, polyglycolides, copolymers of polylactides and polyglycolides, copolymers of lactides and lactones, poly-(ortho)esters, polydioxanone, poly-β-aminoketones, polyphosphazenes, polyanhydrides and polyalkyl-(cyano)acrylates.

2. The ultrasonic contrast agent of claim 1, wherein the microballoons have size in the range of 0.5–10 μm and the membrane is either impervious or permeable to bioactive liquids.

3. The ultrasonic contrast agent of claim 1, wherein the polymer membrane is porous and has porosity ranging from 50 to 2000 nanometers.

4. The ultrasonic contrast agent of claim 1, wherein the membrane polymer is polyglutanic or polyaspartic acid esters or amides and their copolymers with amino acids.

5. The ultrasonic contrast agent of claim 4, wherein the polyglutamic and aspartic acid esters or amides have side functions having formulae

or

or

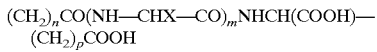

wherein R is an alkyl or aryl substituent; $R^1$ and $R^2$ are H or lower alkyls, or R and $R^1$ are connected together by a substituted or unsubstituted linking member to form a 5- or 6-membered ring; n is 1 or 2; p is 1, 2 or 3; m is an integer from 1 to 5 and X is a side chain of an amino acid residue.

6. The ultrasonic contrast agent of claim 1, wherein the polymer membrane also includes a plasticizer selected from isopropyl myristate and glyceryl monostearate.

7. The ultrasonic contrast agent of claim 1, wherein the polymer membrane also includes a surfactant.

8. The ultrasonic contrast agent of claim 1, wherein the polymer membrane also includes a phospholipid.

9. The ultrasonic contrast agent of claim 1, wherein the polymer membrane also includes a paraffin wax.

10. The ultrasonic contrast agent of claim 1, wherein microballoons are present in the suspension in a concentration of about $10_6$ to $10_{10}$ microballoons per ml.

11. The ultrasonic contrast agent of claim 10, wherein microballoons are present in the suspension in a concentration of about $10^8$ to $10^{10}$ microballoons per ml.

12. The ultrasonic contrast agent of claim 1, wherein the physiologically acceptable gas in the microballoons is selected from the group consisting of $CO_2$, $N_2O$, methane, helium and a freon.

13. The ultrasonic contrast agent of claim 1, wherein the physiologically acceptable gas in the microballoons is a fluorine containing gas.

* * * * *